(12) United States Patent
Passarella

(10) Patent No.: US 11,723,814 B2
(45) Date of Patent: Aug. 15, 2023

(54) METHOD AND APPARATUS FOR PRODUCING ELASTIC LAMINATES

(71) Applicant: Fameccanica.Data S.p.A., San Giovanni Teatino (IT)

(72) Inventor: Fabio Passarella, San Giovanni Teatino (IT)

(73) Assignee: Fameccanica.Data S.p.A., San Giovanni Teatino (IT)

( * ) Notice: Subject to any disclaimer, the term of this patent is extended or adjusted under 35 U.S.C. 154(b) by 0 days.

(21) Appl. No.: 17/837,465

(22) Filed: Jun. 10, 2022

(65) Prior Publication Data

US 2022/0395404 A1 Dec. 15, 2022

(30) Foreign Application Priority Data

Jun. 15, 2021 (EP) .................................... 21179413

(51) Int. Cl.
*A61F 13/15* (2006.01)

(52) U.S. Cl.
CPC .... *A61F 13/15723* (2013.01); *A61F 13/1565* (2013.01); *A61F 13/15764* (2013.01)

(58) Field of Classification Search
None
See application file for complete search history.

(56) References Cited

U.S. PATENT DOCUMENTS

2006/0162843 A1 7/2006 Baldauf et al.
2015/0313774 A1* 11/2015 Homoelle ......... A61F 13/15593
156/192

FOREIGN PATENT DOCUMENTS

EP 0279928 A1 8/1988
EP 3496687 A1 6/2019

OTHER PUBLICATIONS

European Search Report dated Nov. 30, 2021. 4 pages.

* cited by examiner

*Primary Examiner* — Barbara J Musser
(74) *Attorney, Agent, or Firm* — RMCK Law Group PLC

(57) ABSTRACT

A method and apparatus for producing elastic laminates, wherein a first continuous elastic film is stretched in a transverse direction by a spreader device and is applied on a transfer wheel on which it is cut longitudinally to form at least two parallel continuous elastic films which are transferred on a non-woven web held on an outer cylindrical surface of an anvil wheel.

15 Claims, 4 Drawing Sheets

METHOD AND APPARATUS FOR PRODUCING ELASTIC LAMINATES

CROSS-REFERENCE TO RELATED APPLICATION

This application claims priority to European Patent Application No. 21179413.6 filed Jun. 15, 2021. The disclosure of the above application is incorporated herein by reference in its entirety.

FIELD OF THE INVENTION

The present invention relates to a method and an apparatus for producing elastic laminates.

The invention has been developed with particular regard to the production of elastic laminates intended to be used for manufacturing absorbent sanitary articles.

DESCRIPTION OF THE PRIOR ART

For producing absorbent sanitary articles, such as diapers and other absorbent articles, components with different properties are assembled together, such as absorbent cores, backsheets, topsheets, elastic waist bands, elastic side panels, closing formations, elastic barriers for the legs (leg cuffs), etc.

Some components of absorbent sanitary articles, such as elastic bands for the legs, elastic leg barriers, elastic side panels, elastic waist bands, etc., are made from elastic laminates.

Elastic laminates can be produced in various ways depending on the characteristics of the absorbent sanitary articles. For example, some types of elastic laminates may be formed from one or more non-woven webs bonded to an elastic film. In certain applications, the elastic film is stretched in a transverse direction before being fixed between two opposite non-woven webs.

EP3496687 describes a method and an apparatus for assembling elastic laminates wherein a first non-woven web is wound on an outer cylindrical surface of an anvil wheel rotating around a rotation axis, a first and a second elastic film are stretched in a transverse direction on a first and a second spreader device, and are applied on the first non-woven web on the anvil wheel in a first and second application zone displaced axially and angularly relative to each other with respect to the axis of rotation, a second non-woven web is fed to the anvil wheel above the first and second elastic film stretched in the transverse direction, and the first and second non-woven web are welded together ultrasonically through the first and second elastic film and in a central portion comprised between the first and second elastic film.

In the solution described in EP3496687, the first and second elastic film stretched in the transverse direction are transferred from the inclined surfaces of the spreading devices to a non-woven web wound on a cylindrical surface. This creates difficulties in positioning the elastic films as it is difficult to accurately transfer the stretched elastic films from an inclined surface to a cylindrical surface on which a non-woven web is wound. In the solution known from this document, the first and second elastic film, stretched in the transversal direction, are applied to the non-woven web in two areas that are angularly offset from each other. This too causes difficulties in positioning the elastic films with respect to the non-woven web and involves problems in ensuring a precise spacing between the two elastic films.

Other similar solutions are described in EP3496688, EP3496689, EP3496690.

OBJECT AND SUMMARY OF THE INVENTION

The present invention aims to provide a method and apparatus for producing elastic laminates that overcome the problems of the prior art.

According to the present invention, this object is achieved by a method and by an apparatus having the features of claims 1 and 11.

In the solution according to the present invention, the problems of positioning and aligning the stretched elastic films in the transverse direction with respect to the non-woven web are solved due to the fact that the first and second elastic film stretched in the transverse direction are obtained starting from a single continuous elastic film stretched in the transverse direction, applied directly in contact with the outer cylindrical surface of a transfer wheel and cut longitudinally on the transfer wheel. The non-woven web is wound onto the outer cylindrical surface of an anvil wheel, and the first and second elastic film stretched in the transverse direction are applied by the transfer wheel to the non-woven web wound on the anvil wheel in application zones offset from each other in the axial direction and aligned with each other in the angular direction. This solution has the following advantages:

- a single continuous elastic film is transferred from the inclined surfaces of the spreading device to the outer cylindrical surface of the transfer wheel takes place without the interposition of a non-woven web; therefore, the positioning of the stretched continuous elastic film in the transverse direction on the outer cylindrical surface of the transfer wheel takes place with greater precision;
- the stretched elastic films obtained by cutting longitudinally the single continuous elastic film are transferred from the transfer wheel to the non-woven web wound on the outer cylindrical surface of the anvil wheel in application zones aligned with each other in an angular direction; this allows a more precise positioning between the two stretched elastic films in the transverse direction with respect to the non-woven web;
- the application of elastic films stretched in a transversal direction to the non-woven web takes place between two cylindrical surfaces tangent and with respective rotation axes parallel to each other, and this avoids the difficulties due to the transfer on a non-woven web of elastic films stretched in a transverse direction from inclined surfaces to a cylindrical surface.

The method and the apparatus according to the present invention therefore overcome the problems of the solution described in EP3496687.

BRIEF DESCRIPTION OF THE DRAWINGS

The present invention will now be described in detail with reference to the attached drawings, given purely by way of non-limiting example, wherein.

Figure 1:
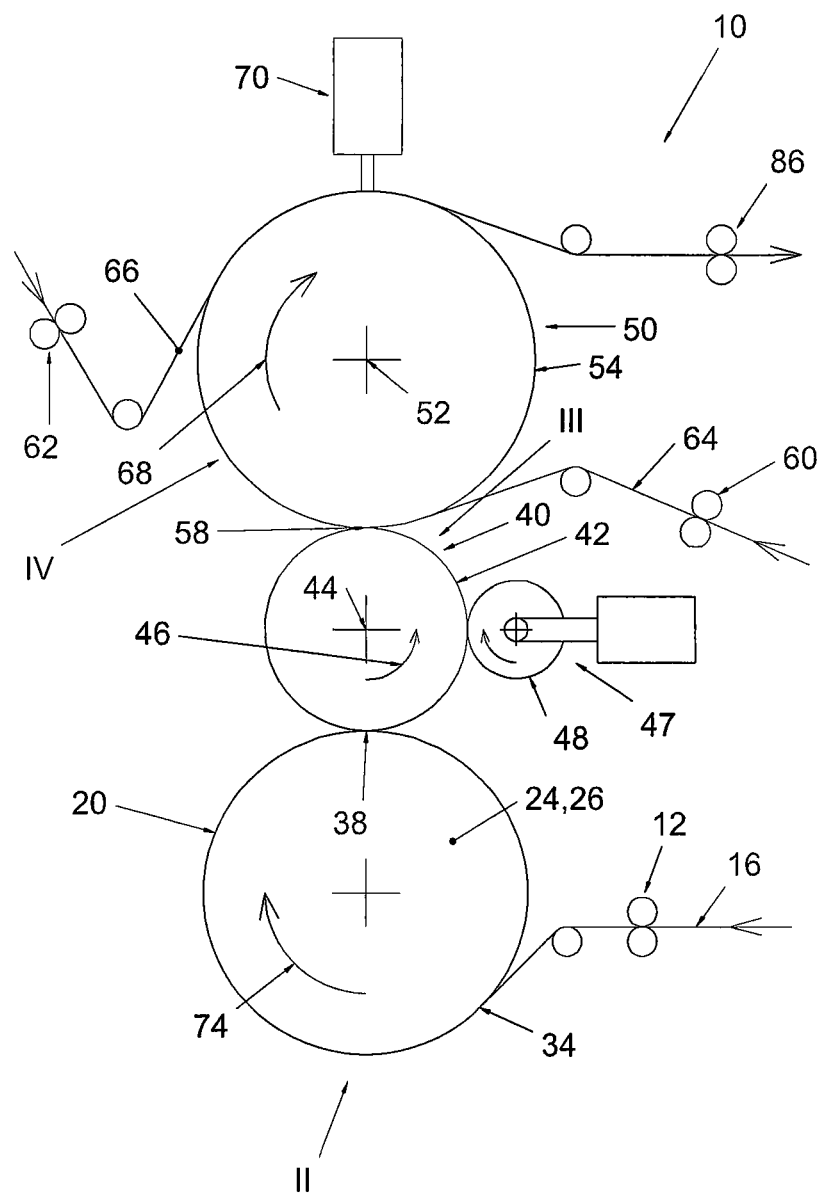
FIG. 1 is a schematic side view of an apparatus according to the present invention.

It will be appreciated that in the drawings some components may not be illustrated to simplify the understanding of the figures, and that various figures may not be represented on the same scale.

DETAILED DESCRIPTION

With reference to FIG. 1, numeral 10 indicates an apparatus for producing elastic laminates.

The apparatus 10 comprises a first feeding device 12 configured to feed a first continuous elastic film 16 in a direction parallel to its longitudinal axis.

The apparatus 10 comprises a spreader device 20 configured to stretch in a transverse direction the first continuous elastic film 16.

Figure 2:
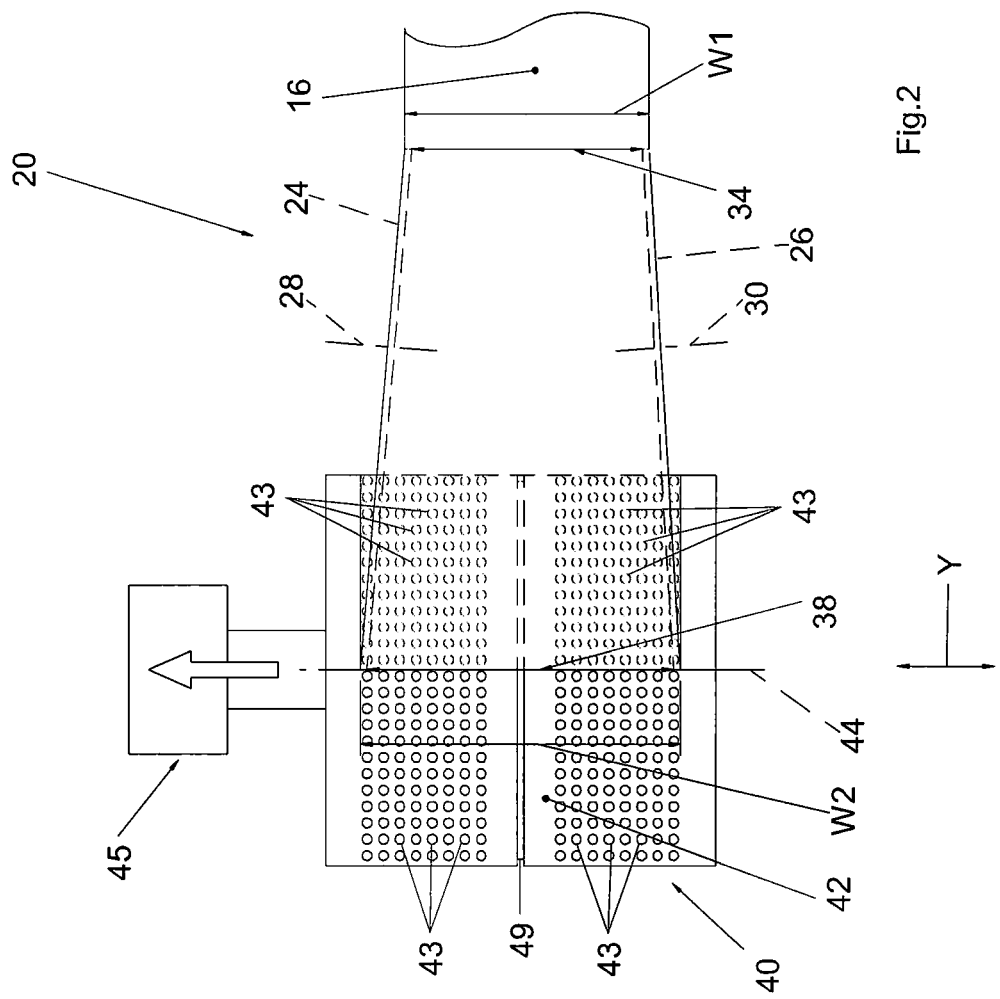
FIGS. 2, 3 and 4 are schematic plan views of the parts indicated by the arrows II, III, and IV in FIG. 1.

With reference to FIG. 2, the spreader device 20 comprises two discs 24, 26 rotatable about respective axes 28, 30 inclined with respect to each other. The discs 24, 26 have respective circumferential edges provided with gripping elements configured to grip respective side edges of the first continuous elastic film 16. In a possible embodiment, the discs 24, 26 may be provided on their circumferential edges with holes connected to a source of sub-atmospheric pressure for gripping the side edges of the elastic film 16 by suction. The circumferential edges of the discs 24, 26 may be provided with protruding pins that engage the side edges of the elastic film 16 alternatively or in addition to the suction holes.

With reference to FIG. 2, the spreader device 20 has a gripping zone 34 and an application zone 38. The discs 24, 26 are spaced from each other in the transverse direction by first distance W1 in the gripping zone 34 and by a second distance W2 greater than the first distance W1 in the application zone 38.

The spreader device 20 picks up the first continuous elastic film 16 in the gripping zone 34 with a first width W1 and releases the first continuous elastic film 16 in the application zone 38 with a second width W2. In the path from the gripping zone 34 to the application zone 38 the elastic film 16 is therefore elastically stretched in a direction Y transverse to the longitudinal axis of the first continuous elastic film 16.

With reference to FIGS. 1 and 2, the apparatus 10 comprises a transfer wheel 40 having an outer cylindrical surface 42. The transfer wheel 40 is rotatable about a first axis of rotation 44 in the direction indicated by the arrow 46 in FIG. 1. The transfer wheel 40 is provided with gripping elements 43 configured to hold the transversally stretched first continuous elastic film 16 on the outer cylindrical surface 42. In a possible embodiment, the gripping elements 43 may consist of holes open on the outer cylindrical surface 42 and pneumatically connected to a source of sub-atmospheric pressure 45, for retaining by suction the transversally stretched first continuous elastic film 16 on the outer cylindrical surface 42. The gripping elements 43 may comprise projecting pins, in addition or in alternative to suction holes.

With reference to FIG. 2, the spreader device 20 applies the transversally stretched first continuous elastic film 16 on the outer cylindrical surface 42 of the transfer wheel 40 in the application zone 38. In the application zone 38 the first continuous elastic film 16 stretched in the transversal direction Y is detached from the discs 24, 26 of the spreader devices 20 and is taken by the gripping elements 43, for example by suction, on the outer cylindrical surface 42 of the transfer wheel 40.

Figure 3:
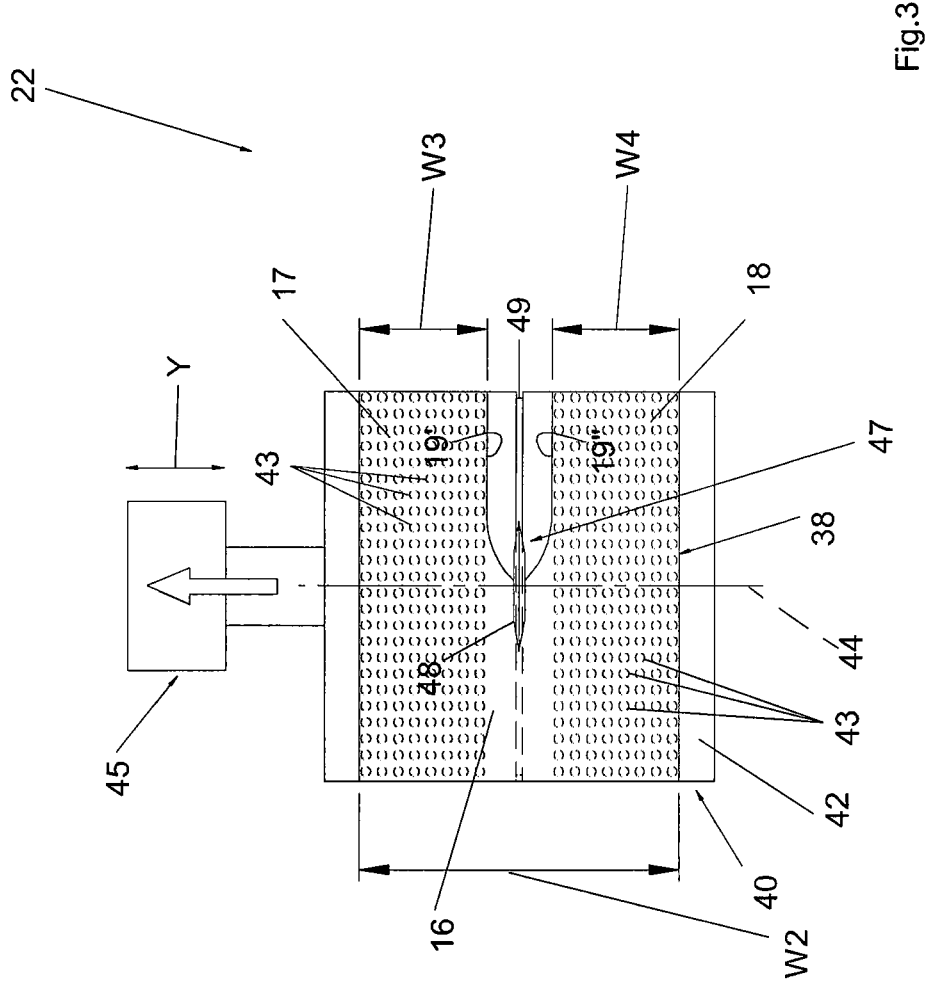

With reference to FIGS. 1 and 3, the apparatus 10 comprises at least one longitudinal cutting device 47 configured to cut along at least one longitudinal cutting line the transversally stretched first continuous elastic film 16 held on the outer cylindrical surface 42 of the transfer wheel 40.

The longitudinal cutting device 47 may comprise a cutting disk 48 rotating about an axis parallel to the axis of rotation of the transfer wheel 40 in a direction opposite to the direction of rotation 46 of the transfer wheel 40. The cutting disk 48 may cooperate with a respective circumferential slot 49 (FIG. 3) formed on the outer cylindrical surface 42 of the transfer wheel 40.

After the longitudinal cut carried out by the longitudinal cutting device 47, the first continuous elastic film 16 is split in at least two parallel continuous elastic films 17, 18, having respective widths W3 and W4. The widths W3 and W4 of the at least two parallel continuous elastic films 17, 18 may be equal or different from each other.

With reference to FIG. 3, after the longitudinal cut of the first continuous elastic film 16, the at least two parallel continuous elastic films 17, 18 may partially contract in the transverse direction Y, so that respective mutually facing longitudinal edges 19', 19" of the at least two parallel continuous elastic films 17, 18 are spaced apart from each other in the transverse direction Y. Accordingly, the sum of the widths W3 and W4 of the at least two parallel continuous elastic films 17, 18 on the outer cylindrical surface 42 of the transfer wheel 40 is less than the with W2 of the first continuous elastic film 16.

The transversal contraction of the at least two parallel continuous elastic films 17, 18 may be obtained by not providing gripping elements 43 (e.g. suction holes and/or protruding pins) on a portion of the outer cylindrical surface 42 of the transfer wheel 40 extending across the cutting line(s), so that the lateral portions of the at least two parallel continuous elastic films 17, 18 adjacent to the cutting line(s) are not retained on the outer cylindrical surface 42 of the transfer wheel 40 and contract elastically in the transverse direction Y.

Figure 4:
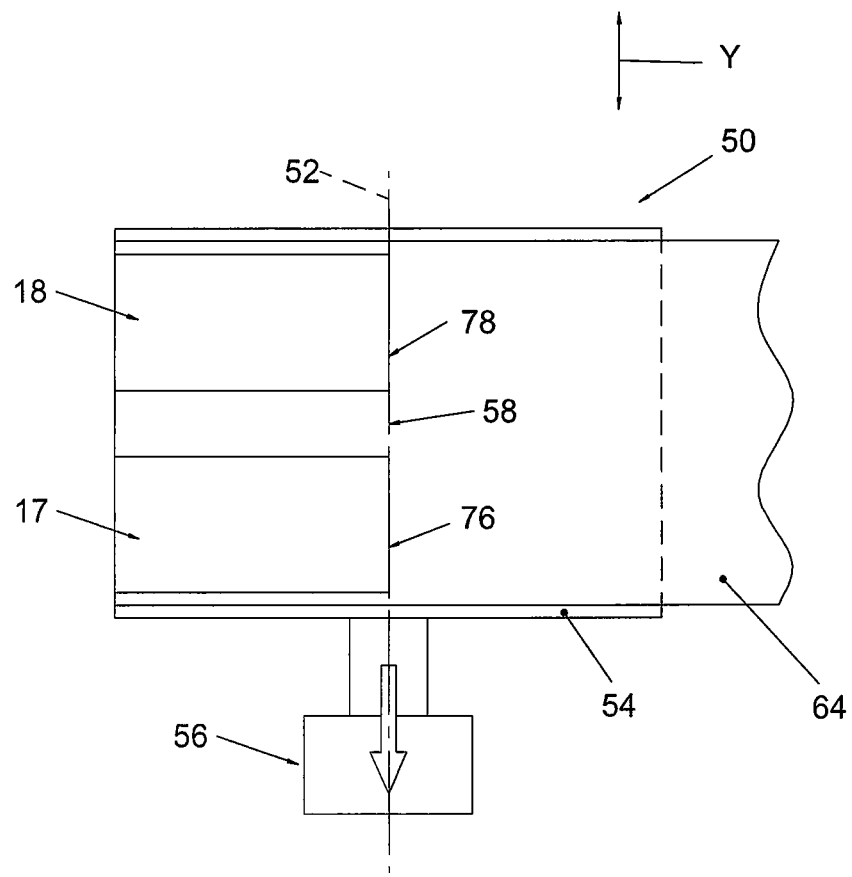

With reference to FIGS. 1 and 4, the apparatus 10 comprises an anvil wheel 50 rotatable about a second axis of rotation 52 parallel to the first axis of rotation 44 of the transfer wheel 40. The anvil wheel 50 has an outer cylindrical surface 54 provided with holes pneumatically connected to a source of sub-atmospheric pressure 56 (FIG. 3). The outer cylindrical surface 54 of the anvil wheel 50 is tangent to the outer cylindrical surface 42 of the transfer wheel 40 in a transfer zone 58.

The apparatus 10 comprises a second feeding device 60 and a third feeding device 62 configured to feed to the anvil wheel a first non-woven web 64 and a second non-woven web 66, respectively. The first non-woven web 64 is applied to the anvil wheel 50 upstream of the transfer zone 58, or at the transfer zone 58, and the second non-woven web 66 is applied to the anvil wheel 50 downstream of the transfer zone 58, with reference to the direction of rotation of the anvil wheel 50 indicated by the arrow 68 in FIG. 1.

The apparatus 10 comprises a fastening device 70 cooperating with the outer cylindrical surface 54 of the anvil wheel 50. The fastening device 70 may be an ultrasonic welding device, a pressure device for fastening by adhesive, or a thermal or thermomechanical welding device.

The operation of the apparatus 10 previously described is as follows.

The first continuous elastic film 16 is unwound from a reel (not shown) and is fed from the feeding device 12 to the spreading devices 20. The first continuous elastic film 16 may be tensioned in the longitudinal direction upstream of the spreading device 20. In the gripping area 34, the lateral edges of the first continuous elastic film 16 are picked up by the discs 24, 26 of the spreader device 20. During the rotation of the discs 24, 26 in the directions indicated by the arrow 74, the first continuous elastic film 16 is stretched in the transverse direction Y. This stretching causes an increase in the width of the elastic film 16 from the value W1 in the gripping zone 34 to the value W2 in the application zone 38 (FIG. 2).

In the application zone 38, the first continuous elastic film 16 stretched in the transverse direction Y is detached from the circumferential edges of the discs 24, 26 and is applied directly in contact with the outer cylindrical surface 42 of the transfer wheel 40.

The first continuous elastic film 16 is kept in a stretched state in a transverse direction Y on the outer cylindrical surface 42 of the transfer wheel 40 by gripping elements 43, e.g. by suction. The fact that the first continuous elastic film 16 (of non-porous material) is applied directly in contact with the outer cylindrical surface 42 of the transfer wheel 40 without the interposition of a layer of porous material allows retaining the first continuous elastic film 16 in a transversally stretched condition with high accuracy.

With reference to FIGS. 1 and 3, after the application of the first continuous elastic film 16 on the outer cylindrical surface 42 of the transfer wheel 40, the first continuous elastic film 16 is cut longitudinally so as to form at least two parallel continuous elastic films 17, 18 which are held in a transversally stretched state on the outer cylindrical surface 42 of the transfer wheel 40. The at least two parallel continuous elastic films 17, 18 may partially contract on the outer cylindrical surface 42 of the transfer wheel 40 so that respective mutually facing longitudinal edges 19', 19" are spaced apart from each other in the transverse direction Y. The at least two parallel continuous elastic films 17, 18 on the outer cylindrical surface 42 of the transfer wheel 40 occupy circumferential bands with respective widths W3, W4 that are spaced apart in a transverse direction Y.

In the embodiment shown in the drawings the first continuous elastic film 16 is cut longitudinally along one longitudinal cutting line so as to form a second and a third continuous elastic film 17, 18.

In a possible embodiment, the first continuous elastic film may be cut longitudinally along a plurality of parallel cutting lines so as to form more than two parallel continuous elastic films. For example, the first continuous elastic film 16 may be cut longitudinally along three parallel cutting lines so as to form four parallel continuous elastic films.

With reference to FIGS. 1 and 4, the first non-woven web 64 is applied to the outer cylindrical surface 54 of the anvil wheel 50 upstream of the transfer zone 58.

The at least two parallel continuous elastic films 17, 18, held in a stretched in the transverse direction on the transfer wheel 42, are applied onto the first non-woven web 64 held on the outer cylindrical surface 54 of the anvil wheel 50.

With reference to FIG. 4, the at least two parallel continuous elastic films 17, 18 are applied onto the first non-woven web 64 on the outer cylindrical surface 54 of the anvil wheel 50 in respective application zones 76, 78 while held in a transversally stretched condition. The application zones 76, 78 are displaced from each other in a transverse direction, and are aligned with each other in the transverse direction Y. The application zones 76, 78 may have the shape of two lines parallel to the axis of rotation 52 and aligned with each other. The fact of applying the at least two parallel continuous elastic films 17, 18 to the first non-woven web 64 along application zones 76, 78 aligned with each other in the transverse direction ensures a high accuracy of mutual positioning between the two elastic films 17, 18. Furthermore, the fact that transferring the at least two parallel continuous elastic films 17, 18 takes place between two cylindrical surfaces with axes parallel to each other simplifies the transfer of the elastic films, and avoids positioning errors that can occur in the case wherein the elastic films are applied on the non-woven web starting from surfaces with inclined axes as occurs in the solution according to the prior art described in EP3496687.

The elastic films 17, 18 are kept on the anvil wheel 50 in a state tensioned in a transverse direction in contact with the first non-woven web 64 by gripping elements, for example by suction.

The gripping elements on the discs 24, 26, on the transfer wheel 42 and on the anvil wheel 50 may comprise holes connected to sources of sub-atmospheric pressure, and/or protruding pins that engage the side edges of the elastic films 17, 18.

After applying the elastic films 17, 18 on the first non-woven web 64 on the outer cylindrical surface 54 of the anvil wheel 50, the second non-woven web 66 is applied on the anvil wheel 50 above the at least two parallel continuous elastic films 17, 18 so that the elastic films 17, 18, tensioned in the transverse direction Y, are sandwiched between the first and the second non-woven web 64, 66.

Then, the two non-woven webs 64, 66 are joined together, for example, by ultrasonic welding, through the at least two parallel continuous elastic films 17, 18 by the fastening device 70.

Joining the two non-woven webs 64, 66 to each other through the at least two parallel continuous elastic films 17, 18 includes both the direct fastening of the two webs through openings in the elastic film, and the fastening of the two webs comprising the elastic film between them.

The fastening device 70 may be configured to form a plurality of connecting points that form respective holes passing through the elastic films 17, 18, and that directly fix the two opposite non-woven webs 64, 66 to each other through the holes formed in the elastic films 17, 18. The elastic films 17, 18 remain anchored to the non-woven webs 64, 66 at the connecting points that extend through the holes formed in the elastic films 17, 18. This solution provides breathable elastic laminates thanks to the formation of holes passing through the elastic films 17, 18.

The two non-woven webs 64, 66 may be fixed directly to each other in portions comprised between the at least two parallel continuous elastic films 17, 18, and along the longitudinal edges external to elastic films 17, 18.

The fastening device 70 may be configured to carry out a uniform fastening pattern over the entire surface of the non-woven webs 64, 66, both at the elastic films 17, 18 and in the areas that do not contain the elastic films 17, 18.

Figure 5:
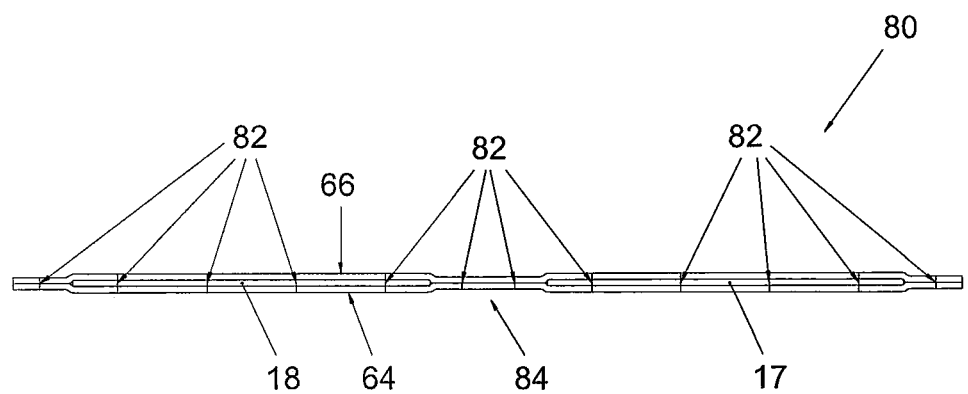
FIG. 5 is a schematic cross-section of an elastic laminate obtained with an apparatus according to the present invention.

Downstream of the fastening device 70, an elastic laminate is obtained having the shape schematically illustrated in FIG. 5, comprising at least two parallel continuous elastic films 17, 18 enclosed between two non-woven webs 64, 66, and anchored to the two non-woven webs 64, 66 by a pattern of connecting points 82. The elastic laminate 80 has at least one portion 84 wherein the elastic films 17, 18 are spaced apart from each other and the two non-woven webs 64, 66 are in direct contact with each other.

The portion(s) 84 of the elastic laminate 80 may be cut in the longitudinal direction by a longitudinal cutting device indicated schematically by 86 in FIG. 1. The longitudinal cutting device 86 may carry out at least one continuous through-cut so as to give rise to separate elastic bands, each comprising an elastic film 17, 18 anchored between two non-woven webs 64, 66. In a possible embodiment, the longitudinal cutting device 86 may make at least one longitudinal weakening line in the portion 84 of the elastic laminate 80 that constitutes a preferential breaking line, which allows two or more elastic bands to be detached from each other following the application of a weak detaching force.

In another embodiment of the present invention, the first non-woven web 64 may be applied to the outer cylindrical surface 54 of the anvil wheel 50 at the transfer zone 58, for example, by first being applied to the transfer wheel 40, above the at least two transversally stretched elastic films 17, 18 between the second application zone 38 and the transfer zone 58.

As compared to the prior art, the apparatus and method according to the present invention has the following advantages:
1. full control of longitudinal cutting of the first continuous elastic film, not hindered by the presence of a non-woven web;
2. possibility of applying low percentage of transverse elongation to the elastic films;
3. use of a single spreader device, a single unwinder for the elastic film, a single feeding device for the elastic film;
4. the longitudinal cut of the film under tension is simpler and less contaminating;
5. elimination of the risk that the non-woven webs can be damaged by the film cutting process;
6. elastic films formed after cutting the continuous elastic film which can have different widths, if required.

Of course, without prejudice to the principle of the invention, the details of construction and the embodiments can be widely varied with respect to those described and illustrated, without thereby departing from the scope of the invention as defined by the claims that follow.

The invention claimed is:

1. A method for producing elastic laminates, comprising:
feeding a first continuous elastic film,
stretching the first continuous elastic film in a transverse direction,
applying the first continuous elastic film on an outer circumferential surface of a transfer wheel rotatable around a first axis of rotation,
holding the first continuous elastic film transversally stretched on said outer circumferential surface of the transfer wheel,
cutting longitudinally the transversally stretched first continuous elastic film on said outer circumferential surface of the transfer wheel so as to split the first continuous elastic film into at least two parallel continuous elastic films,
holding said at least two parallel continuous elastic films in a transversally stretched state on said outer circumferential surface of the transfer wheel,
applying a first non-woven web on an outer cylindrical surface of an anvil wheel rotatable around a second axis of rotation parallel to the first axis of rotation,
transferring said at least two parallel continuous elastic films from the transfer wheel onto the first non-woven web held on the outer cylindrical surface of the anvil wheel,
applying a second non-woven web on the anvil wheel above said at least two parallel continuous elastic films, and
forming an elastic laminate by joining the first and second non-woven webs through said at least two parallel continuous elastic films.

2. The method of claim 1, wherein after cutting longitudinally the transversally stretched first continuous elastic film on said outer circumferential surface, said at least two parallel continuous elastic films partially contract in a transverse direction, so that respective mutually facing longitudinal edges of the at least two parallel continuous elastic films are spaced apart from each other in said transverse direction.

3. The method of claim 2, wherein lateral portions of said at least two parallel continuous elastic films adjacent to said mutually facing longitudinal edges are not retained on the outer cylindrical surface of the transfer wheel so that said lateral portions contract in said transversal direction.

4. The method of claim 1, wherein the first continuous elastic film is cut longitudinally along three parallel longitudinal cutting lines, so as to form four parallel continuous elastic films.

5. The method of claim 1, wherein the first continuous elastic film is cut longitudinally so as to form a plurality of parallel continuous elastic films having a same width.

6. The method of claim 1, wherein the first continuous elastic film is cut longitudinally so as to form a plurality of parallel continuous elastic films having different widths.

7. The method of claim 1, comprising transferring said at least two parallel continuous elastic films onto the first non-woven web held on the outer cylindrical surface of the anvil wheel along two application zones in a form of lines parallel to the second axis of rotation of the anvil wheel and aligned with each other.

8. The method of claim 1, comprising joining to each other the first and second non-woven webs according to a uniform pattern both at said at least two parallel continuous elastic films and in at least one portion comprised between said at least two parallel elastic films.

9. The method of claim 1, comprising cutting in a longitudinal direction at least one portion of the elastic laminate comprised between said at least two parallel continuous elastic films.

10. The method of claim 1, comprising forming at least one longitudinal weakening line in at least one portion of the elastic laminate comprised between said at least two parallel continuous elastic films.

11. An apparatus for producing elastic laminates, comprising:
a first feeding device configured to feed a first continuous elastic film,
a spreader device configured to stretch the first continuous elastic film in a transverse direction,
a transfer wheel rotatable around a first axis of rotation and having an outer cylindrical surface, wherein said spreader device is configured to apply the first continuous elastic film stretched in the transverse direction on the outer circumferential surface of the transfer wheel,
gripping elements provided on said outer cylindrical surface of said transfer wheel configured to hold the first continuous elastic film transversally stretched on said outer circumferential surface of said transfer wheel,
at least one longitudinal cutting device configured to cut said first continuous elastic film on said outer circumferential surface of the transfer wheel, so as to split the first continuous elastic film into at least two parallel continuous elastic films, an anvil wheel rotatable around a second axis of rotation parallel to the first axis of rotation, wherein the transfer wheel is tangent to the anvil wheel in a transfer zone, and is configured to transfer said at least two parallel continuous elastic films to the anvil wheel, a second feeding device configured to feed a first non-woven web on the outer cylindrical surface of the anvil wheel upstream of said transfer zone, or at said transfer zone, a third feeding device configured to feed a second non-woven web to the anvil wheel downstream of said transfer zone, and a fixing unit cooperating with the anvil wheel and configured to join to each other the first and second non-woven webs through said at least two parallel continuous elastic films.

12. The apparatus of claim 11, wherein said at least one longitudinal cutting device comprises a cutting disk rotating about an axis parallel to the first axis of rotation of the transfer wheel and cooperating with a respective circumferential slot formed on the outer cylindrical surface of the transfer wheel.

13. The apparatus of claim 11, wherein said gripping elements comprise suction holes and/or projecting pins.

14. The apparatus of claim 11, wherein said gripping elements are not provided on a portion of the outer cylindrical surface of the transfer wheel extending across at least one cutting line.

15. The apparatus of claim 11, comprising three longitudinal cutting devices configured to cut said first continuous elastic film on said outer circumferential surface of the transfer wheel along three parallel cutting lines, so as to split the first continuous elastic film into four parallel continuous elastic films.

* * * * *

UNITED STATES PATENT AND TRADEMARK OFFICE
CERTIFICATE OF CORRECTION

PATENT NO. : 11,723,814 B2
APPLICATION NO. : 17/837465
DATED : August 15, 2023
INVENTOR(S) : Fabio Passarella It is certified that error appears in the above-identified patent and that said Letters Patent is hereby corrected as shown below:

On the Title Page

Column 1, (71) Applicant address information should be listed as:
- Fameccanica.Data S.p.A., San Giovanni Teatino (Chieti), ITALY -

Column 1, (72) Inventor address information should be listed as:
- Fabio Passarella, San Giovanni Teatino (Chieti), ITALY -

Column 1, (73) Assignee address information should be listed as:
- Fameccanica.Data S.p.A., San Giovanni Teatino (Chieti), ITALY -

Signed and Sealed this
Twenty-sixth Day of March, 2024

Katherine Kelly Vidal
*Director of the United States Patent and Trademark Office*